(12) United States Patent
Gruber et al.

(10) Patent No.: US 10,393,697 B2
(45) Date of Patent: Aug. 27, 2019

(54) APPARATUS FOR ANALYZING ION KINETICS IN DIELECTRICS

(71) Applicant: Infineon Technologies AG, Neubiberg (DE)

(72) Inventors: Sabine Gruber, Reifnitz (AT); Thomas Aichinger, Villach (AT); Stefan Krivec, Arnoldstein (AT); Thomas Ostermann, Velden am Woerthersee (AT)

(73) Assignee: Infineon Technologies AG, Neubiberg (DE)

( * ) Notice: Subject to any disclaimer, the term of this patent is extended or adjusted under 35 U.S.C. 154(b) by 301 days.

(21) Appl. No.: 14/930,295

(22) Filed: Nov. 2, 2015

(65) Prior Publication Data

US 2016/0139077 A1    May 19, 2016

(30) Foreign Application Priority Data

Nov. 3, 2014   (DE) .................. 10 2014 115 980

(51) Int. Cl.
| | |
|---|---|
| *G01N 27/447* | (2006.01) |
| *G01N 27/453* | (2006.01) |
| *G01N 27/27* | (2006.01) |
| *G01N 27/414* | (2006.01) |

(52) U.S. Cl.
CPC ....... *G01N 27/44704* (2013.01); *G01N 27/27* (2013.01); *G01N 27/453* (2013.01); *G01N 27/414* (2013.01)

(58) Field of Classification Search
USPC ........................................ 257/253
See application file for complete search history.

(56) References Cited

U.S. PATENT DOCUMENTS

| | | | | |
|---|---|---|---|---|
| 4,232,326 A | * | 11/1980 | Neidig | G01N 27/414 257/253 |
| 5,747,839 A | | 5/1998 | Hammond et al. | |
| 8,035,175 B2 | * | 10/2011 | Shim | G01N 27/4145 257/225 |

(Continued)

FOREIGN PATENT DOCUMENTS

| | | |
|---|---|---|
| DE | 10151021 A1 | 4/2003 |
| DE | 10216614 A1 | 10/2003 |
| DE | 102013102289 A1 | 10/2013 |

OTHER PUBLICATIONS

Sun et al. (Phys. Chem. Chem. Phys., 16, 7455) (Year: 2014).*

(Continued)

*Primary Examiner* — Gurpreet Kaur
*Assistant Examiner* — Steven E Rosenwald
(74) *Attorney, Agent, or Firm* — Murphy, Bilak & Homiller, PLLC

(57) ABSTRACT

An apparatus for analyzing ion kinetics in a dielectric probe structure includes an ion reservoir abutting the dielectric probe structure and configured to supply mobile ions to the dielectric probe structure, a capacitor structure configured to generate an electric field in the dielectric probe structure along a vertical direction, and an electrode structure configured to generate an electrophoretic force on mobile ions in the dielectric probe structure along a lateral direction. A method for analyzing ion kinetics in the dielectric probe structure of the apparatus is also provided.

24 Claims, 13 Drawing Sheets

(56) References Cited

U.S. PATENT DOCUMENTS

| | | | |
|---|---|---|---|
| 2005/0062093 A1* | 3/2005 | Sawada | G01N 27/4145 |
| | | | 257/316 |
| 2008/0134759 A1 | 6/2008 | Mohammed-Brahim et al. | |
| 2013/0234761 A1 | 9/2013 | Weber et al. | |
| 2014/0055145 A1* | 2/2014 | Krivec | G01N 27/414 |
| | | | 324/459 |

OTHER PUBLICATIONS

Mobile Ionic Contamination (EESemi.com) (Year: 2018).*
Young et al. (J. Appl. Phys. 66(1), 187) (Year: 1989).*
Liu et al. (Chem. Mater. 25, 3788-3796) (Year: 2013).*

* cited by examiner

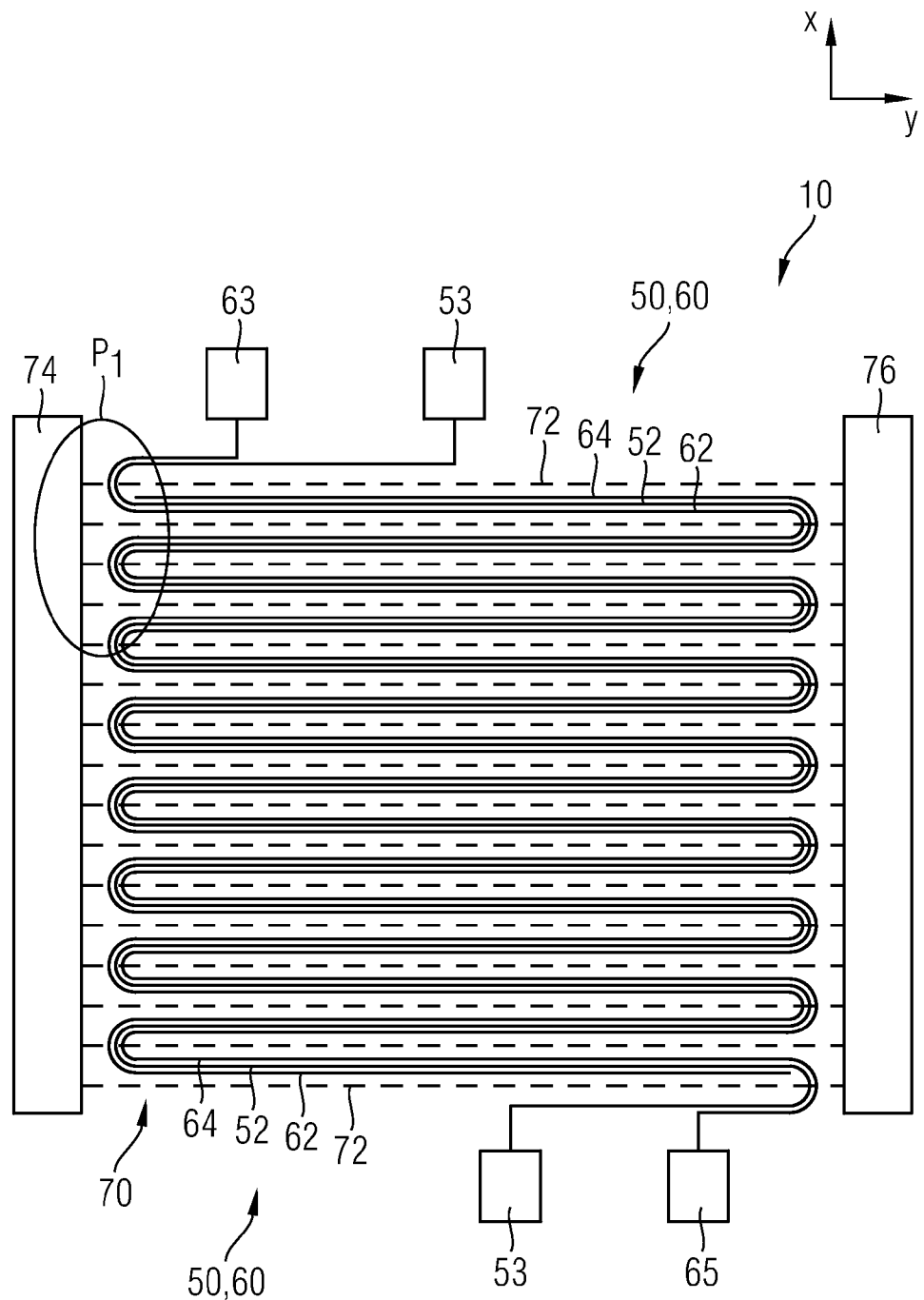

APPARATUS FOR ANALYZING ION KINETICS IN DIELECTRICS

PRIORITY CLAIM

This application claims priority to German Patent Application No. 10 2014 115 980.2 filed on 3 Nov. 2014, the content of said application incorporated herein by reference in its entirety.

BACKGROUND

Measuring the quantitative concentration of mobile ions in a liquid sample may be accomplished by chromatographic or spectroscopic methods such as, for instance HPLC (High-performance or high pressure liquid chromatography), AAS (Atomic absorption spectroscopy) or ICP-MS (Inductively coupled plasma mass spectrometry). Further approaches with electric response signals are available, for example ISFET (Ion sensitive field effect transistors) or derivatives thereof. Each approach has advantages in terms of ease of use and sensitivity, enabling the measurement of mobile ion down to a magnitude of ppm or even lower. These methods require large and expensive apparatus and specially trained staff.

In the health care industry testing of human blood samples is often carried out. As one example, a blood sample may be tested for the presence of K+(potassium ions), which may be carried out using one or more of the above-described techniques. Such techniques may require a relatively long amount of time and/or substantial cost to perform.

For modelling and calibration of semiconductor devices, which are configured to measure physiological or chemical sample characteristics such as concentration and composition of ion solution samples, a thorough understanding of drift and diffusion behavior of mobile ions in dielectrics is desirable.

SUMMARY

According to an embodiment of an apparatus for analyzing ion kinetics in a dielectric probe structure, the apparatus comprises an ion reservoir abutting the dielectric probe structure and configured to supply mobile ions to the dielectric probe structure, a capacitor structure configured to generate an electric field in the dielectric probe structure along a vertical direction, and an electrode structure configured to generate an electrophoretic force on mobile ions in the dielectric probe structure along a lateral direction.

According to an embodiment of a method for analyzing ion kinetics in the dielectric probe structure of the apparatus described above, the method comprises applying an electrophoretic force on mobile ions in the dielectric probe structure along the lateral direction, and determining an electric characteristic of the capacitor structure based on the presence of mobile ions in the dielectric probe structure.

Those skilled in the art will recognize additional features and advantages upon reading the following detailed description and on viewing the accompanying drawings.

BRIEF DESCRIPTION OF THE DRAWINGS

The accompanying drawings are included to provide a further understanding of embodiments of the invention and are incorporated in and constitute a part of this specification. The drawings illustrate the embodiments of the present invention and together with the description serve to explain the principles. Other embodiments of the invention and many of the intended advantages will be readily appreciated, as they become better understood by reference to the following detailed description. The elements of the drawings are not necessarily to scale relative to each other. Like reference numbers designate corresponding similar parts.

FIG. 6A is a schematic plan view of a portion of an apparatus for analyzing ion kinetics in a dielectric probe structure according to another embodiment.

DETAILED DESCRIPTION

Figure 1A:
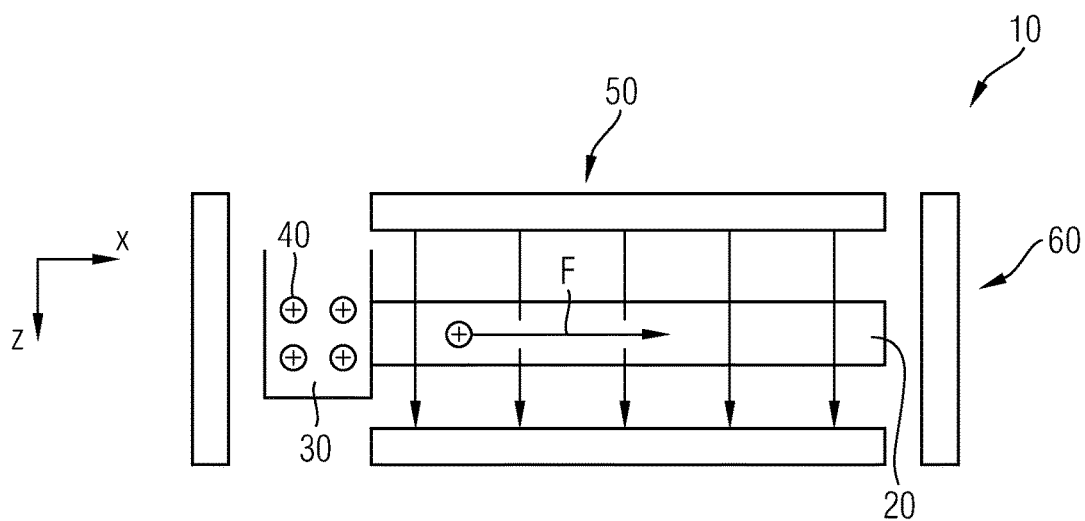
FIG. 1A is a schematic view of an apparatus for analyzing ion kinetics in a dielectric probe structure according to an embodiment.

In the following detailed description reference is made to the accompanying drawings, which form a part hereof and in which are illustrated by way of illustration specific embodiments in which the invention may be practiced. In this regard, directional terminology such as "top", "bottom", "front", "back", "leading", "trailing" etc. is used with reference to the orientation of the Figures being described. Since components of embodiments of the invention can be positioned in a number of different orientations, the directional terminology is used for purposes of illustration and is in no way limiting. It is to be understood that other embodiments may be utilized and structural or logical changes may be made without departing from the scope defined by the claims.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The Figures and the description illustrate relative doping concentrations by indicating "−" or "+" next to the doping type "n" or "p". For example, "n−" means a doping concentration which is lower than the doping concentration of an "n"-doping region while an "n+"-doping region has a higher doping concentration than an "n"-doping region. Doping regions of the same relative doping concentration do not necessarily have the same absolute doping concentration. For example, two different "n"-doping regions may have the same or different absolute doping concentrations. In the Figures and the description, for the sake of a better comprehension, often the doped portions are designated as being "p" or "n"-doped. As is clearly to be understood, this designation is by no means intended to be limiting. The doping type can be arbitrary as long as the described functionality is achieved. Further, in all embodiments, the doping types can be reversed.

As employed in this specification, the terms "coupled" and/or "electrically coupled" are not meant to mean that the elements must be directly coupled together—intervening elements may be provided between the "coupled" or "electrically coupled" elements. The term "electrically connected" intends to describe a low-ohmic electric connection between the elements electrically connected together.

The present specification refers to a "first" and a "second" conductivity type of dopants, semiconductor portions are doped with. The first conductivity type may be p type and the second conductivity type may be n type or vice versa. As is generally known, depending on the doping type or the polarity of the source and drain regions, MOSFETs may be n-channel or p-channel MOSFETs. For example, in an n-channel MOSFET, the source and the drain region are doped with n-type dopants, and the current direction is from the drain region to the source region. In a p-channel MOSFET, the source and the drain region are doped with p-type dopants, and the current direction is from the source region to the drain region. As is to be clearly understood, within the context of the present specification, the doping types may be reversed. If a specific current path is described using directional language, this description is to be merely understood to indicate the path and not the polarity of the current flow, i.e. whether the transistor is a p-channel or an n-channel transistor. The Figures may include polarity-sensitive components, e.g. diodes. As is to be clearly understood, the specific arrangement of these polarity-sensitive components is given as an example and may be inverted in order to achieve the described functionality, depending whether the first conductivity type means n-type or p-type.

The terms "lateral" and "horizontal" as used in this specification intends to describe an orientation parallel to a first surface of a semiconductor substrate or semiconductor body. This can be for instance the surface of a wafer or a die.

The term "vertical" as used in this specification intends to describe an orientation which is arranged perpendicular to the first surface of the semiconductor substrate or semiconductor body.

The terms "wafer", "substrate" or "semiconductor body" used in the following description may include any semiconductor-based structure that has a semiconductor surface. Wafer and structure are to be understood to include silicon, silicon-on-insulator (SOI), silicon-on sapphire (SOS), doped and undoped semiconductors, epitaxial layers of silicon supported by a base semiconductor foundation, and other semiconductor structures. The semiconductor need not be silicon-based. The semiconductor could as well be silicon-germanium, germanium, or gallium arsenide. According to other embodiments, silicon carbide (SiC) or gallium nitride (GaN) may form the semiconductor substrate material.

It is to be understood that the features of the various embodiments described herein may be combined with each other, unless specifically noted otherwise.

FIG. 1A is a schematic block diagram of an apparatus 10 for analyzing ion kinetics in a dielectric probe structure 20 according to an embodiment.

Figure 1B:
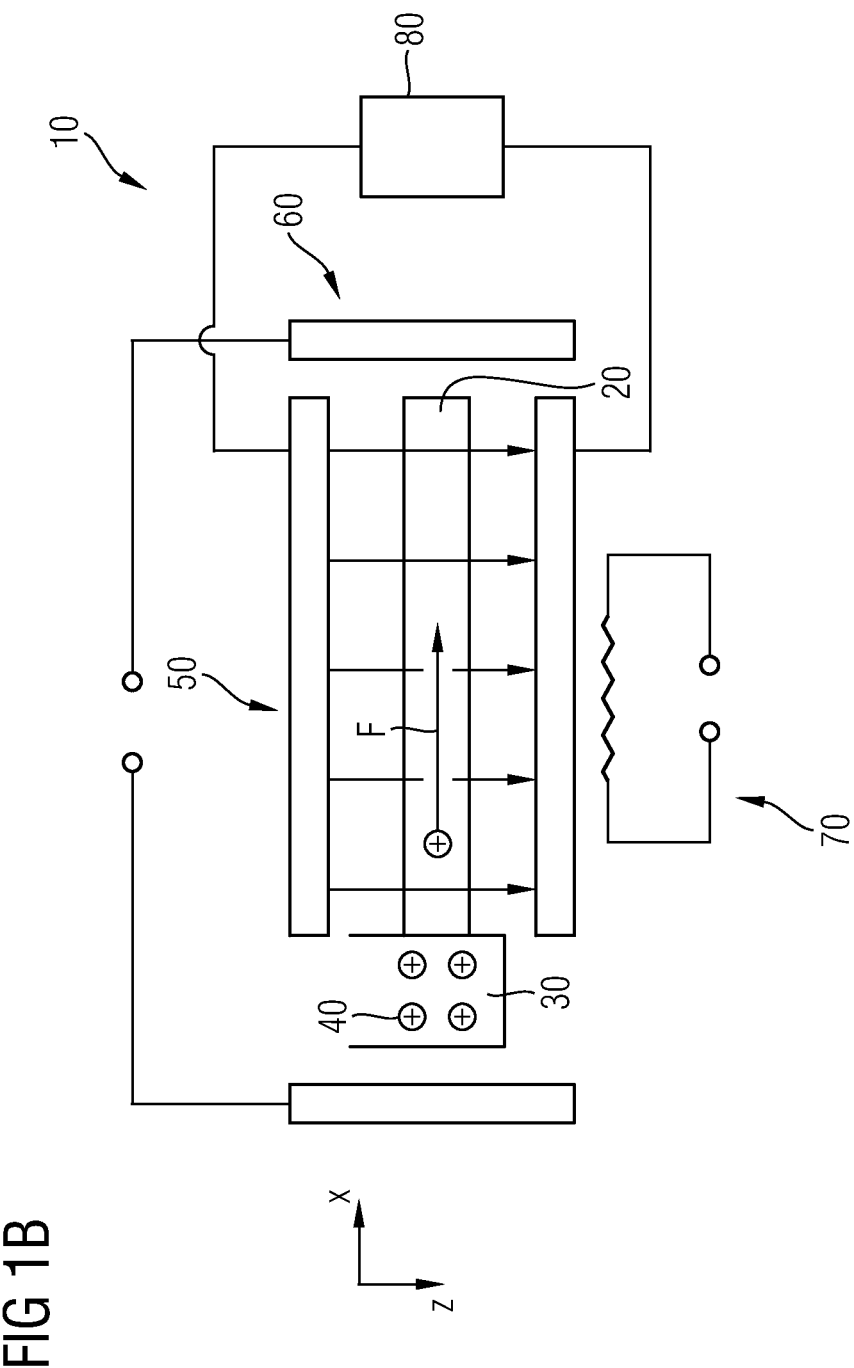
FIG. 1B is a schematic view of an apparatus for analyzing ion kinetics in a dielectric probe structure according to another embodiment.

The apparatus 10 for analyzing ion kinetics in the dielectric probe structure 20 comprises an ion reservoir 30 abutting the dielectric probe structure 20 for supplying mobile ions 40 to the dielectric probe structure 20. The mobile ions 40 move through the dielectric probe structure 20 in a lateral direction x by means of an electrophoretic force F, which is generated by an electrode structure 60. Herein, the electrode structure 60 is configured to generate the electrophoretic force F on mobile ions 40 in the dielectric probe structure 20 along the lateral direction x. Further, a capacitor structure 50 is configured to generate an electric field in the dielectric probe structure 20 along a vertical direction z. Herein, a processing unit 80 (FIG. 1B) may be provided for determining an electric characteristic of the capacitor structure 50 in dependence on the presence of mobile ions 40 in the dielectric probe structure 20. For setting a defined temperature of the dielectric probe structure 20, a heater 70 may be employed, as illustrated in FIG. 1B. Thus, a well-defined measurement environment is provided, in which the dielectric properties of the dielectric probe structure 20 can be determined while mobile ions 40 drift through the dielectric probe structure 20 in a lateral direction x.

Figure 2:
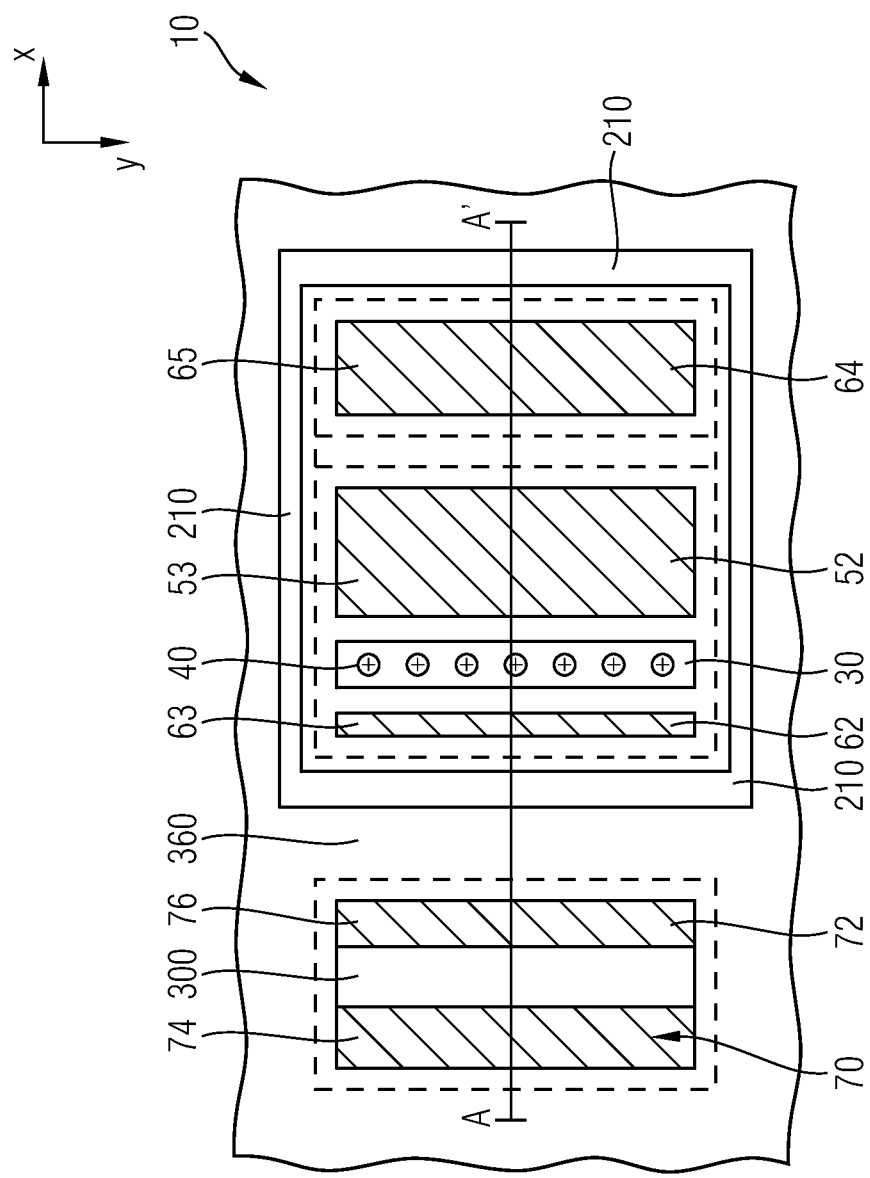
FIG. 2 is a schematic plan view of a portion of an apparatus for analyzing ion kinetics in a dielectric probe structure according to an embodiment.
Figure 3A:
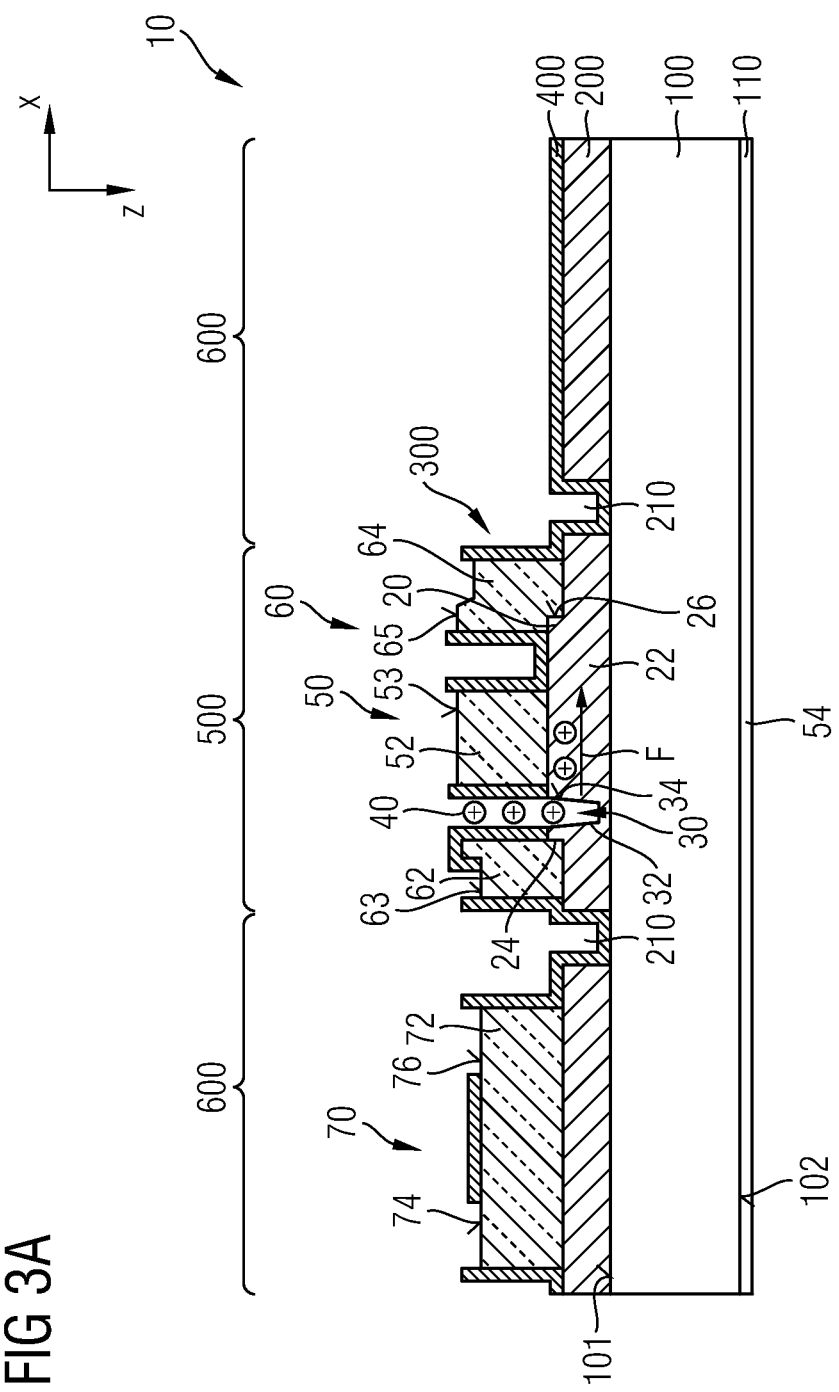
FIG. 3A is a schematic cross-sectional view of a portion of the apparatus for analyzing ion kinetics taken along the section plane A-A' of FIG. 2.

FIG. 2 shows a schematic plan view of a portion of an apparatus 10 for analyzing ion kinetics in the dielectric probe structure 20 according to an embodiment, and FIG. 3A is a schematic cross-sectional view of a portion of apparatus 10 for analyzing ion kinetics taken along the section plane A-A' of FIG. 2.

As shown in FIGS. 2 and 3A, the apparatus 10 includes a semiconductor body 100. The semiconductor body 100 includes a semiconductor material, for example silicon Si, silicon carbide SiC, germanium Ge, silicon germanium SiGe, gallium nitride GaN or gallium arsenide GaAs. The semiconductor body 100 may include a semiconductor layer structure having one or more semiconductor layer(s), e.g. epitaxial layer(s) on a semiconductor substrate. Outside the illustrated portion, the semiconductor body 100 may include, inter alia, further doped and undoped sections, semiconductor layers, insulating and conducting structures, or edge terminations such as planar edge termination structures or mesa edge termination structures, for example. The semiconductor body 100 has a first surface 101 and a second surface 102 which is opposite to the first surface 101.

On the first surface 101, a dielectric structure 200 is formed. The dielectric structure 200 may have a thickness along the vertical direction z in a range between 100 nm and 1 μm. The dielectric structure 200 may include one or any combination of an oxide, a nitride, oxynitride, a high-K material, a low-k material, an imide, an insulating resin or glass such as a tetraethylorthosilicate (TEOS/undoped silicate glass (USG)) or a phosphosilicate glass (PSG) or borophosphosilicate glass (BPSG), for example. The dielectric structure 200 may also comprise silicon oxide $SiO_2$, silicon oxynitride $SiO_xN_y$, or amorphous silicon nitride containing hydrogen or deuterium $a\text{-}Si_xN_yH_z/Si_xN_yD_z$. The dielectric structure 200 may include any dielectric or a combination of dielectrics to be probed in view of its ion transport characteristics.

On the dielectric structure 200, a patterned electrode layer structure 300 is formed. The patterned electrode layer structure 300 may contain one, two, three or more sub-layers, each sub-layer containing, as a main constituent, at least one of nickel Ni, titanium Ti, silver Ag, gold Au, tungsten W, platinum Pt and palladium Pd. For example, a sub-layer may contain a metal nitride or a metal alloy containing Ni, NiV, Ti, Ag, Au, W, Pt, and/or Pd. The patterned electrode layer structure 300 may also consist of or contain, as a main constituent(s) aluminium Al, copper Cu or alloys of aluminium or copper, for example AlSi, AlCu, or AlSiCu. A thickness of the patterned electrode layer structure 300 may be in a range of 500 nm to 10 μm. The patterned electrode layer structure 300 may also comprise a conductive semiconductor material such as a highly doped polysilicon material.

On the patterned electrode layer structure 300, the patterned dielectric structure 200 and the first surface 101 of the semiconductor body 100, a diffusion barrier layer 400 is formed. The diffusion barrier layer 400 may comprise a material being configured to prevent diffusion of mobile ions through the diffusion barrier layer 400 such as silicon nitride, for example. A thickness of the diffusion barrier layer 400 may be in a range of 200 nm to 800 nm, for example.

On the second surface 102, a back electrode 54 of the capacitor structure 50 may be formed by a back electrode layer 110. The back electrode layer 110 may comprise the same material or material composition such as the patterned electrode layer structure 300.

In the following, the structure of the apparatus 10 for analyzing ion kinetics in the dielectric probe structure 20 will be explained. On the first surface 101 of the semiconductor body 100, a first part 500 of the apparatus 10 and a second part 600 of the apparatus 10 are formed. The dielectric structure 200 of the first part 500 is separated from the dielectric structure 200 of the second part 600 by a ring trench 210 (FIGS. 2 and 3A). The inner wall of the ring trench 210 is lined by the diffusion barrier layer 400. The trench 210 can reduce or prevent a diffusion of the mobile ions 40 into the dielectric structure 200 of the second part 600. It is, however, also possible to provide the trench 210 only in the lateral direction x.

In the second part 600 of the apparatus 10, the heater 70 comprising a heating conductive layer 72 being part of the patterned electrode layer structure 300 may be provided to heat the dielectric probe structure 20. Thus, the dielectric probe structure 20 may be heated by the heater 70. The heating operation may be performed by supplying an electric current through the heating conductive layer 72 of the heater 70 to generate heat caused by the resistance of the conductive material. The heat of the heater 70 is thermally conducted through the dielectric structure 200 of the second part 600 to the semiconductor body 100, and then to the dielectric structure 200 in the first part 500. The heater 70 may further comprise a heating conductive layer 72 of polycrystalline silicon. The structure of the heater 70 may be configured depending on the structure of the first part 500. The heater 70 may be, for example, be arranged in a ring form surrounding the first part 500. Furthermore, the heater 70 may be arranged in a meander form to increase the length of the heating conductive layer 72 and thus the generated heat for heating the first part 500. Additional embodiments of the heater 70 in view of the first part 500 will be described with regard to FIGS. 6A to 6D and 7A to 7C.

The first part 500 of the apparatus 10 comprises the dielectric probe structure 20, the ion reservoir 30, the capacitor structure 50 and the electrode structure 60. The capacitor structure 50 comprises the semiconductor body 100, the dielectric probe structure 20 on the semiconductor body 100, and a capacitor electrode 52 on the dielectric probe structure 20. Herein, the capacitor structure 50 further comprises a dielectric base structure 22 between the semiconductor body 100 and the dielectric probe structure 20. In detail, the dielectric structure 200 of the first part 500 of the apparatus 10 comprises the dielectric base structure 22 and, on the dielectric base structure 22, the dielectric probe structure 20. The dielectric probe structure 20 and the dielectric base structure 22 are parts of the dielectric structure 200 in the first part 500, wherein the dielectric probe structure 20 is a patterned dielectric body protruding along the vertical direction z from the dielectric base structure 22.

The dielectric probe structure 20 has a first side wall 24 and a second side wall 26, between which the mobile ions 40 are forced to move in the lateral direction x. For generating an electrophoretic force F on the mobile ions 40, the electrode structure 60 comprises a first electrode 62 located next to the ion reservoir 30 at the first side wall 24 of the dielectric probe structure 20 and a second electrode 64 located at the second lateral side 26 of the dielectric probe structure 20.

As can be seen from FIG. 3A, the thickness of the dielectric structure 200 in the second part 600 and the thickness of the dielectric base structure 22 in the first part 500 is the same, wherein the dielectric probe structure 20 protrudes from the dielectric base structure 22 in a step form having the side walls 24, 26. The first and second electrodes 62, 64 for generating the electrophoretic force F on the mobile ions 40 are part of the patterned electrode layer structure 300 and are thus formed on the dielectric structure 200 comprising the dielectric base structure 22 and the dielectric probe structure 20. As a consequence, a lower part of the first and the second electrodes 62, 64 is on the same vertical level as the dielectric probe structure 20, which makes it possible to generate a lateral electrical field from the first electrode 62 to the second electrode 64 through the dielectric probe structure 20.

The capacitor electrode 52, which is, together with the first and second electrodes 62 and 64, part of the patterned electrode layer structure 300, is formed on the top surface of the dielectric probe structure 20 between the first side wall and the second side wall 26, to determine the electric characteristics of the dielectric probe structure 20 in the vertical direction z being orthogonal to the moving direction of the mobile ions 40, which is the lateral direction x. The dimension of the dielectric probe structure 20 in the lateral direction x may be in a range of 1 μm to 200 μm, or in a range of 10 μm to 100 μm, and a dimension of the dielectric probe structure 20 in the vertical direction z may be in a range of 10 nm to 1 μm, or in a range of 200 nm to 600 nm.

The ion reservoir 30 comprises a cavity 32, which is extended through the dielectric probe structure 20 along the vertical direction z. The cavity 32 of the ion reservoir 30 is configured to receive a liquid or solid solution of the mobile ions 40. The cavity 32 has the diffusion barrier layer 400 lining the inner wall of the cavity 32 and at least one ion access area 34 providing access for the mobile ions 40 to the dielectric probe structure 20. According to one embodiment, the ion access area 34 may be an area arranged to enable the mobile ions 40 to come into substantially direct contact with the dielectric probe structure 20. In an embodiment, the ion access area 34 may be an area within the inner wall of the cavity 32, in which the diffusion barrier layer 400 is absent. In another embodiment, the ion access area 34 may comprise a protective layer that is permeable at least for mobile ions 40 which are to be detected. For example, a protective layer that is permeable to potassium ions may be used while larger ions or lager molecules can be blocked. Thus, a selective analysis of ion transport characteristic in the dielectric probe structure 20 using a selective sort of ions may be achieved. The liquid ion solution may be an aqueous ion solution. Herein, the mobile ions 40 may be one of a group consisting of $H^+$, $Li^+$, $Na^+$, $K^+$, $Ca^{++}$, $Mg^{++}$. Further, the mobile ions 40 may be one of a group consisting of $Cl^-$, $F^-$, or $OH^-$.

Figure 3B:
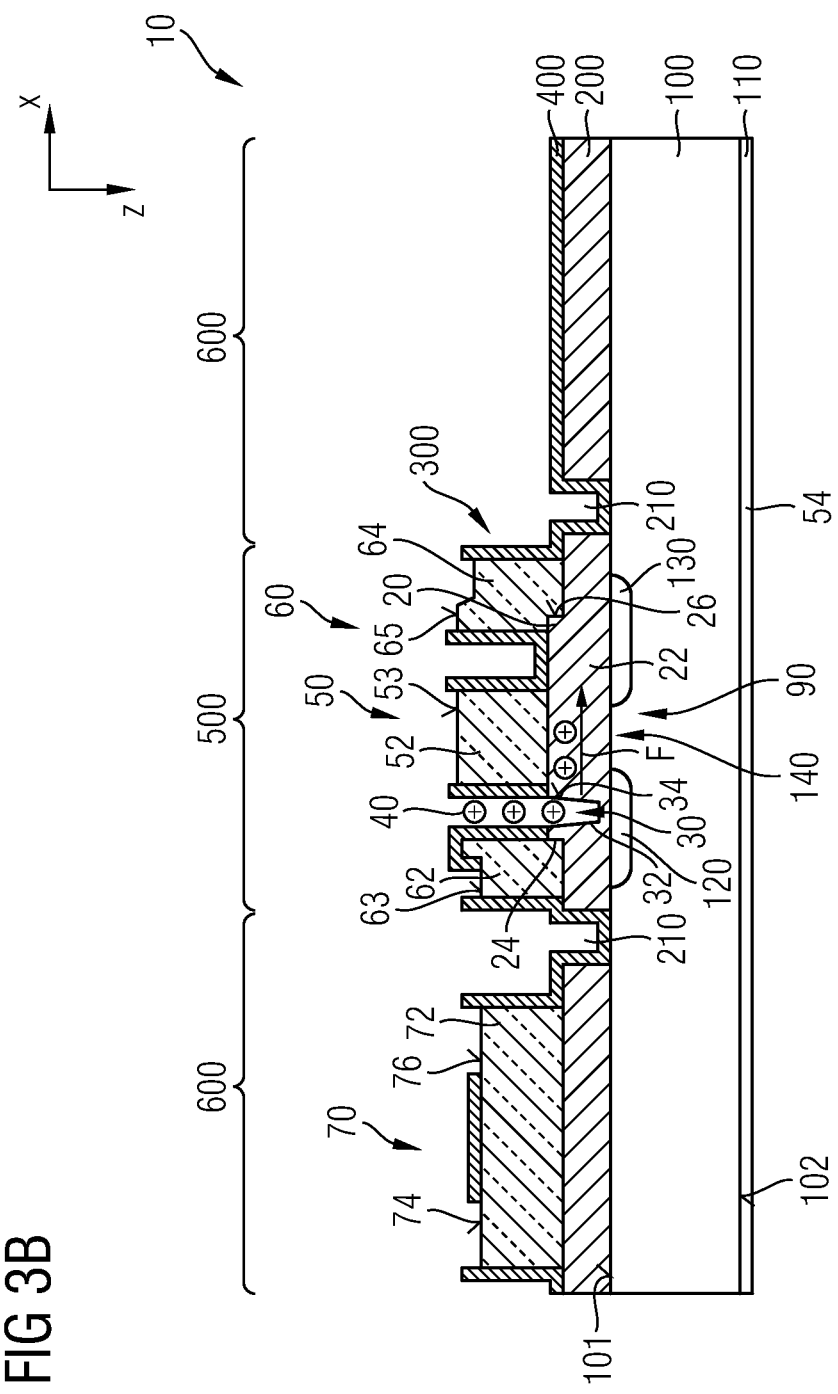
FIG. 3B is a schematic cross-sectional view of a portion of the apparatus for analyzing ion kinetics taken along the section plane A-A' of FIG. 2, further comprising a MISFET-structure.

FIG. 3B is a schematic cross-sectional view of a portion of the apparatus 10 for analysing ion kinetics taken along the section plane A-A' of FIG. 2, further comprising a Metal Insulator Semiconductor Field Effect Transistor (MISFET)-structure 90. Those features of the embodiment of FIG. 3B being similar to the features of the embodiment of FIG. 3A will not be described again and reference is drawn to the details given above.

As can be seen from FIG. 3B, the capacitor structure 50 further comprises the Metal Insulator Semiconductor Field Effect Transistor (MISFET)-structure 90 having a source region 120 and a drain region 130 formed in the semiconductor body 100, wherein the dielectric probe structure 20 acts as the gate dielectric of the MISFET-structure 90, and the capacitor electrode 52 acts as the gate electrode of the MISFET-structure 90. The back electrode 54 may be used to electrically contact the bulk region of the MISFET-structure 90. By applying an electrical field between the gate electrode (the capacitor electrode 52) and the semiconductor body 100, a channel region 140 in the semiconductor body 100 at the boundary region between the gate dielectric (the dielectric probe structure 20) and the semiconductor body 100 (i.e. the first surface 101) may be formed between the source region 120 and the drain region 130 along the lateral direction x, resulting in a source-drain current of the MISFET structure 90. By means of the MISFET-structure 90, an influence of the mobile ions 40 being present and moving along a lateral direction x in the dielectric probe structure 20 (acting as the gate dielectric) on the source-drain current in the channel region 140 of the MISFET-structure 90 may be analyzed. For example, the presence of the mobile ions 40 within the dielectric probe structure 20 may shift the threshold voltage of the MISFET-structure 90, resulting in the possibility to determine the presence and/or amount of mobile ions 40 in the dielectric probe structure 20 overlapping the channel region 140. The capacitor electrode 52 may also be omitted in the embodiment of FIG. 3A, wherein a lateral current through the dielectric probe structure 20 between the first electrode 62 and the second electrode 64 may be measured. In this case, the diffusion barrier layer 400 may be extended continuously from the ion reservoir 30 to the second electrode 64 on the dielectric probe structure 20.

Figure 4:
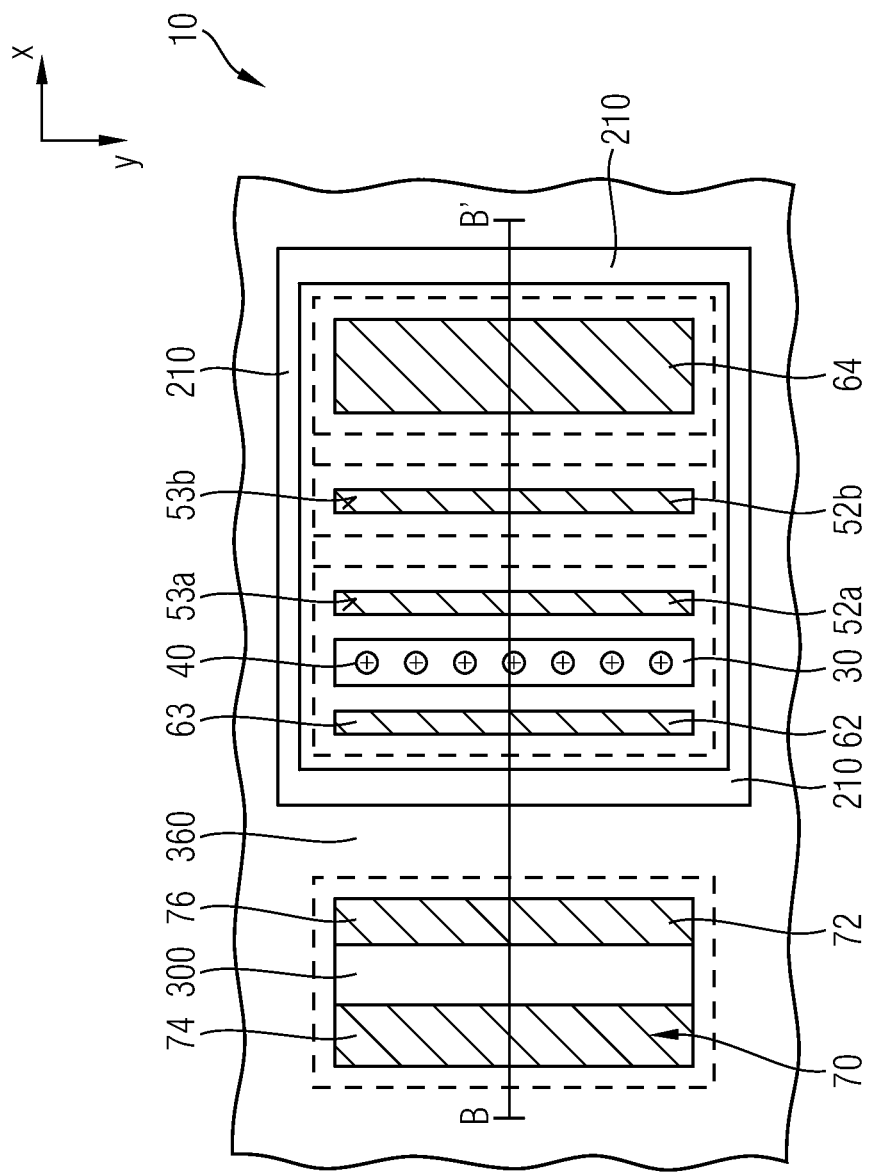
FIG. 4 is a schematic plan view of a portion of an apparatus for analyzing ion kinetics in a dielectric probe structure according to another embodiment.
Figure 5:
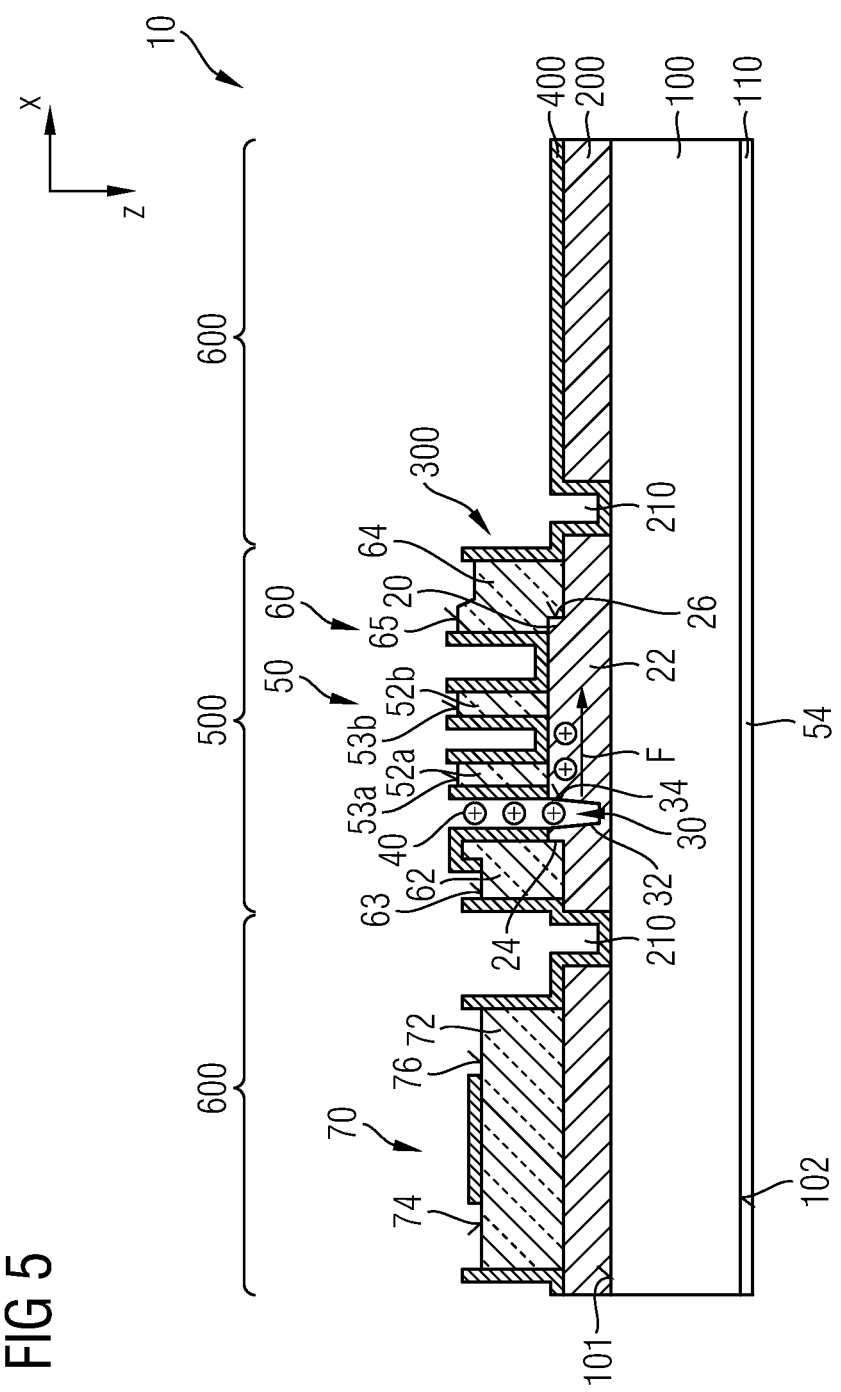
FIG. 5 is a schematic cross-sectional view of a portion of the apparatus for analyzing ion kinetics taken along the section plane B-B' of FIG. 4.

FIG. 4 is a schematic plan view of a portion of an apparatus 10 for analyzing ion kinetics in the dielectric probe structure 20 according to another embodiment, wherein FIG. 5 is a schematic cross-sectional view of the portion of the apparatus 10 along the section plane B-B' of FIG. 4. Those features of the embodiments of FIGS. 4 and 5 being similar to the features of the embodiments of FIGS. 2 and 3A will not be described again and reference is drawn to the details given above.

According to the embodiment of FIG. 4 and FIG. 5, the capacitor electrode 52 is separated into two capacitor electrode parts 52a, 52b in a lateral direction x. In other words, the capacitor electrode 52 comprises at least two capacitor electrode parts 52a, 52b each being separated in the lateral direction x. Thus, at least two capacitor electrode parts 52a, 52b of the capacitor electrode 52 may be provided to measure the electric characteristics of the dielectric probe structure 20 in a vertical direction z orthogonal to the moving direction x of the mobile ions 40 in the dielectric probe structure 20. As a result, the analysis of ion kinetics in the dielectric probe structure 20 may be improved by detecting certain groups of mobile ions 40 in respective parts being covered by the capacitor electrode parts 52a, 52b of the capacitor electrode 52. Although not shown, at least two MISFET-structures as shown in FIG. 3A (MISFET-structure 90) may be integrated in the structure of FIG. 5, wherein the at least two capacitor electrode parts 52a, 52b act as gate electrodes for the respective MISFET-structures.

In the following, a method for manufacturing the apparatus 10 of FIGS. 2 to 5 will be described. In a first step, a dielectric structure 200 is formed on the first surface 101 of the semiconductor body 100.

Then, a recess step by means of, for example a plasma etching process is performed to form a step in the dielectric structure 200. By means of the exemplary plasma etching process, the dielectric probe structure 20 is formed to protrude from the dielectric base structure 22.

Thereafter, the trench 210 is formed, which extends through the dielectric structure 200 to the first surface 101 of the semiconductor body 100, to prevent diffusion of mobile ions 40 in the dielectric structure 200 over the complete dielectric structure 200, i.e. to maintain the mobile ions 40 within the first part 500 of the apparatus 10.

By depositing and patterning of the electrode layer structure 300 by means of a wet etching process, the heating conductive layer 72, the first electrode 62, the capacitor electrode 52 (or the parts 52a, 52b of the capacitor electrode 52 in FIGS. 4 and 5), and the second electrode 60 are formed.

For preventing intrusion of mobile ions into the apparatus 10, the complete patterned structure of the semiconductor body 100, the dielectric structure 200, and the patterned electrode structure 300 is covered by depositing the diffusion barrier layer 400.

For providing connection terminals 74, 76 to the heating conductive layer 72, a connection terminal 63 to the first electrode 62, a connection terminal 53 to the capacitor electrode 52 (or connection terminals 53a, 53b to the at least two capacitor electrode parts 52a, 52b in FIGS. 4 and 5), a connection terminal 65 to the second electrode 64, and the ion access area 34, the diffusion barrier layer 400 is selectively removed by means of a plasma etching process. As can be seen from FIGS. 3A, 3B and 5, the cavity 32 does not extend to the first surface 101 to ensure an electrochemical insulation between the semiconductor body 100 and the ion reservoir 30. However, the plasma etching process may be used at the same time to form the cavity 32 in the dielectric structure 200 being extended to the first surface 101 of the semiconductor body 100, the semiconductor body 100 acting as an etching stop layer for the anisotropic plasma etching process. Thus, a well-defined and clean boundary area for supplying mobile ions into the dielectric probe structure 20 can be achieved. Thereafter, an insulating layer for insulating the ion reservoir 30 from the semiconductor body 100 may be provided.

FIG. 6A is a schematic plan view of a portion of an apparatus 10 for analyzing ion kinetics in a dielectric probe structure 20 according to another embodiment.

As can be seen from FIG. 6A, the capacitor structure 50 and the electrode structure 60 may be arranged in a meander form, wherein the heater 70 is arranged between the meander path of the capacitor structure 50 and the electrode structure 60. In particular, the apparatus 10 comprises the first connection terminal 74 and the second connection terminal 76 of the heater 70, wherein the heating conductive layer 72 of polycrystalline silicon is arranged in parallel stripes being extended from the first connection terminal 74 to the second connection terminal 76 along a lateral direction y being orthogonal to the lateral direction x. The capacitor electrode 52 may be connected by two connection terminals 53 at a boundary part of the region of the parallel stripes of the heating conductive layer 72. The capacitor electrode 52 runs in parallel to the stripes of the heating conductive layer 72 in a meander form. In other words, the capacitor electrode 52 runs reciprocally between the first connection terminal 74 and the second connection terminal 76 of the heater 70 in a meander form. The electrode structure 60 comprising the first electrode 62 and the second electrode 64 is arranged in parallel to the capacitor electrode 52 in a meander form.

In detail, the first electrode 62 is arranged to run parallel to the capacitor electrode 52 on a first side of the capacitor electrode 52 and the second electrode 64 is arranged to run parallel to the capacitor electrode 52 on the other side of the capacitor electrode 52. As a consequence, the apparatus 10 is formed such that the first part 500 as shown for example in FIG. 3A, FIG. 3B is arranged in a meander form. The first electrode 62 may be connected by the connection terminal 63 and the second electrode 64 may be connected by the connection terminal 65, which are arranged in a boundary part of the region of the heater 70.

Figure 6B:
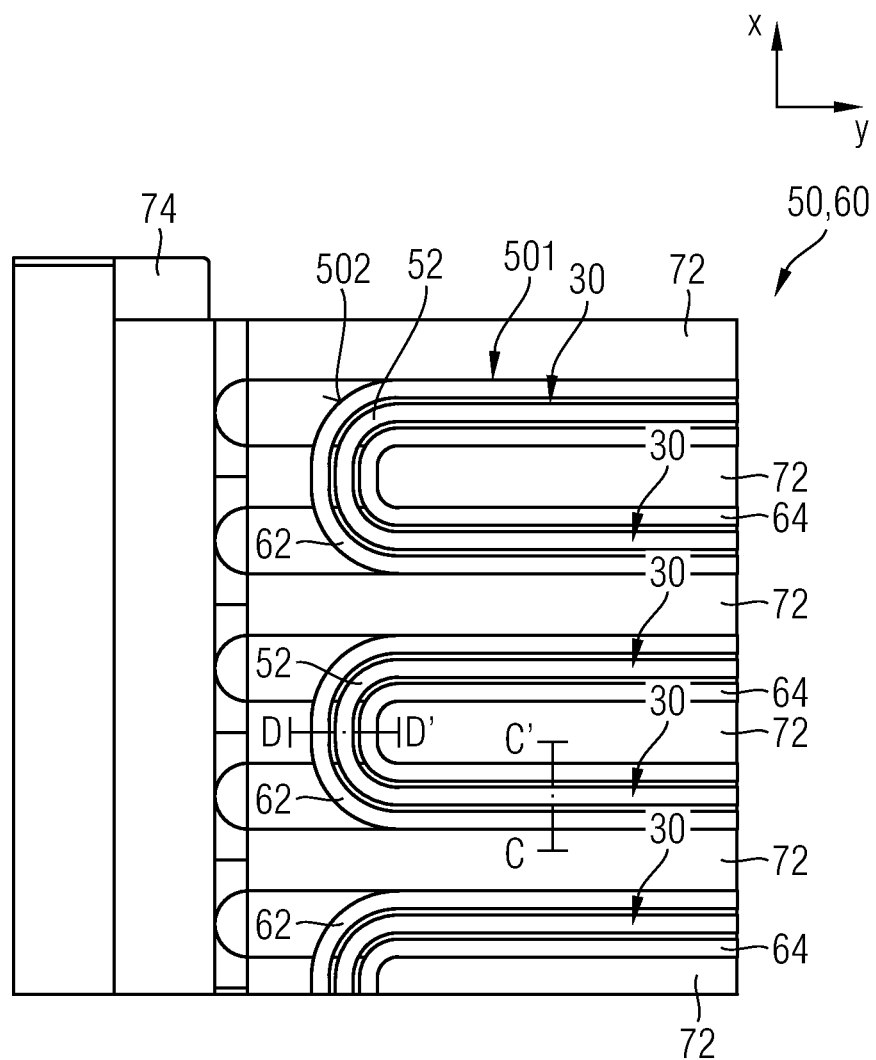
FIG. 6B is a detailed plan view of part $P_1$ of FIG. 6A.

As can be seen from FIG. 6B, which is a detailed view of the part $P_1$ of FIG. 6A, the meander form of the first electrode 62, the capacitor electrode 52 and the second electrode 64 comprises a straight part 501 being arranged parallel to the stripes of the heating conductive layer 72 and a bend part 502, in which the electrodes 62, 52 and 64 are bend to connect the nth and the (n+1)th straight part 501 of the electrodes 62, 52 and 64 along the lateral direction x, wherein n is an odd number. The straight part 501 further comprises the dielectric probe structure 20 and the ion reservoir 30 and is thus comparable to the structure as shown for example in the first part 500 of FIG. 3A. On the side of the second connection terminal 76 (not shown in detail), a further bend part exists, which connects the (n+1)th straight part 501 with the (n+2)th straight part 501, wherein n is an odd number.

Figure 6C:
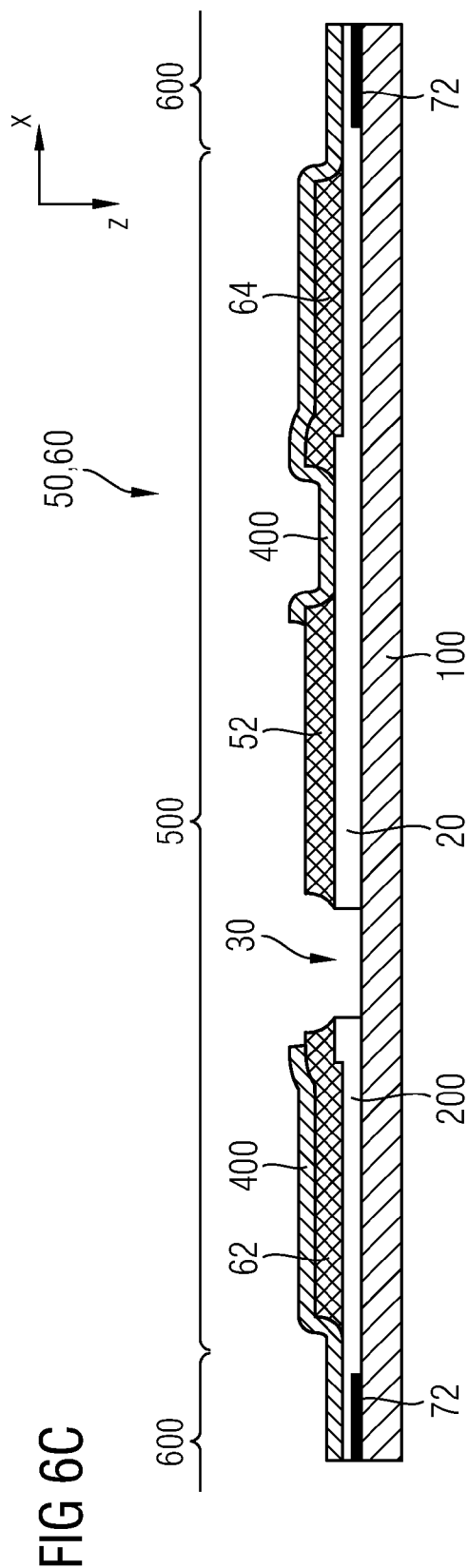
FIG. 6C is a schematic cross-sectional view of a portion of the apparatus for analyzing ion kinetics taken along the section plane C-C' of FIG. 6B.
Figure 6D:
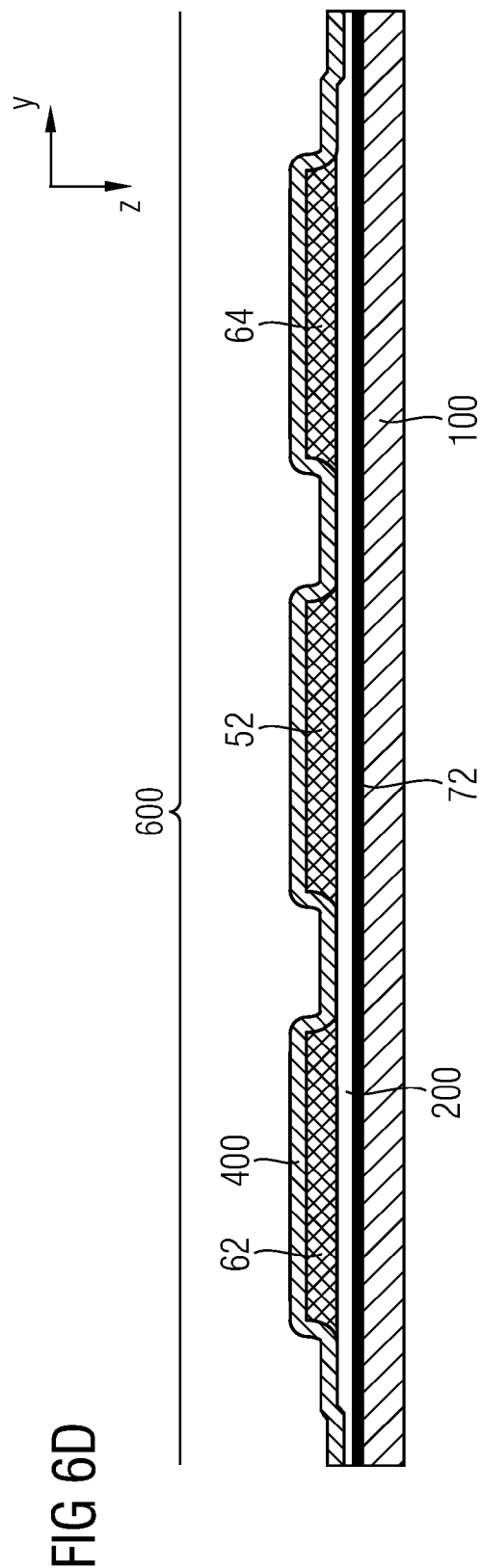
FIG. 6D is a schematic cross-sectional view of a portion of the apparatus for analyzing ion kinetics taken along the section plane D-D' of FIG. 6B.

As can be seen from the schematic cross-sectional views of the portion of the apparatus 10 for analyzing ion kinetics taken along the section plane D-D' in FIG. 6C and taken along the section plane C-C' in FIG. 6D, the stripes of the heating conductive layer 72 are arranged such that they are neighbored to the straight parts 501 of the electrodes 62, 52 and 64 in a lateral direction y (cf. FIG. 6C) and cross the bend parts 502 of the electrodes 62, 52 and 64 at a side portion next to the first connection terminal 74 (and in an analogous way in a side portion next to the second connection terminal 76). Thus, a current from the first connection terminal 74 through the stripes of the heating conductive layer 72 to the second connection terminal 76 of the heater 70 leads to a homogeneous heating of the dielectric probe structure 20 of the apparatus 10.

Figure 7A:
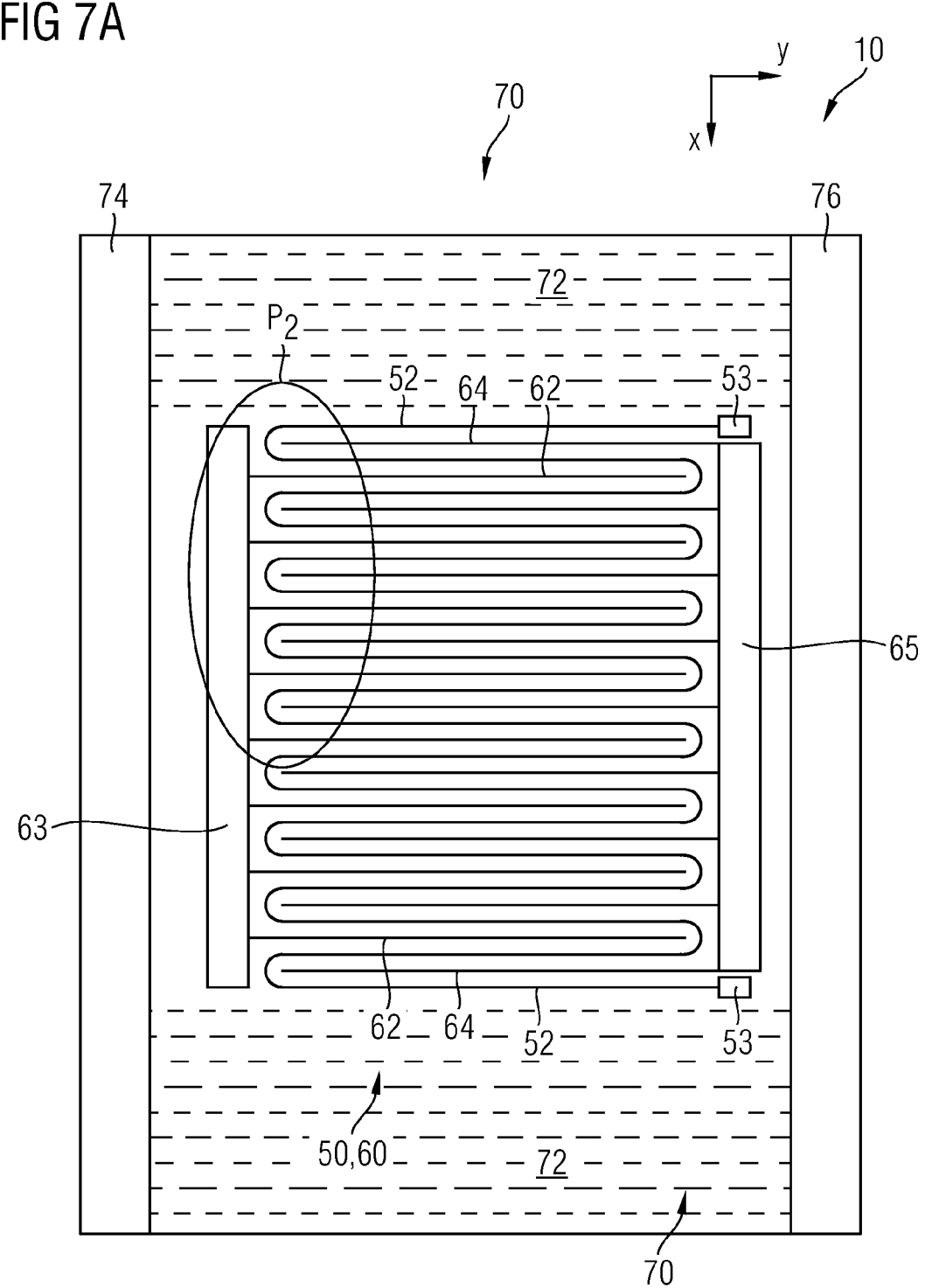
FIG. 7A is a schematic plan view of a portion of an apparatus for analyzing ion kinetics in a dielectric probe structure according to another embodiment.

FIG. 7A is a schematic plan view of a portion of an apparatus 10 for analyzing ion kinetics in a dielectric probe structure 20 according to another embodiment.

As can be seen from FIG. 7A, the structure of the capacitor electrode 52 having the connection terminals 53 is comparable to the structure as described with regard to FIG. 6A, in which the capacitor structure 50 is arranged in a meander form. The structure of the apparatus 10 of FIG. 7A differs from the structure as shown in FIG. 6A in that the electrode structure 60 comprises two finger electrode structures interlacing with each other in parallel, and further interlacing with the capacitor structure 50 being arranged in a meander form. In detail, the first electrode 62 comprises a plurality of parallel electrode stripes forming a finger structure extending from the connection terminal 63 along the lateral direction y. In addition, the second electrode 64 comprises a plurality of parallel electrode stripes forming a finger structure extending from the connection terminal 65 along the lateral direction y such that the electrode stripes of the first electrode 62 and the electrode stripes of the second electrode 64 interlace with each other.

The capacitor electrode 52 is arranged such in a meander form that it runs reciprocally between the electrode stripes of the first electrode 62 and the second electrode 64. The heater 70 is arranged such that the electrode structure 50, 60 is embedded into the heater 70. In detail, the heating conductive layer 72 is arranged between the first connection terminal 74 and the second connection terminal 76 such that a current in the lateral direction y heats the heating conductive layer 72 being neighbored to the electrode structure 60 and the capacitor structure 50.

Figure 7B:
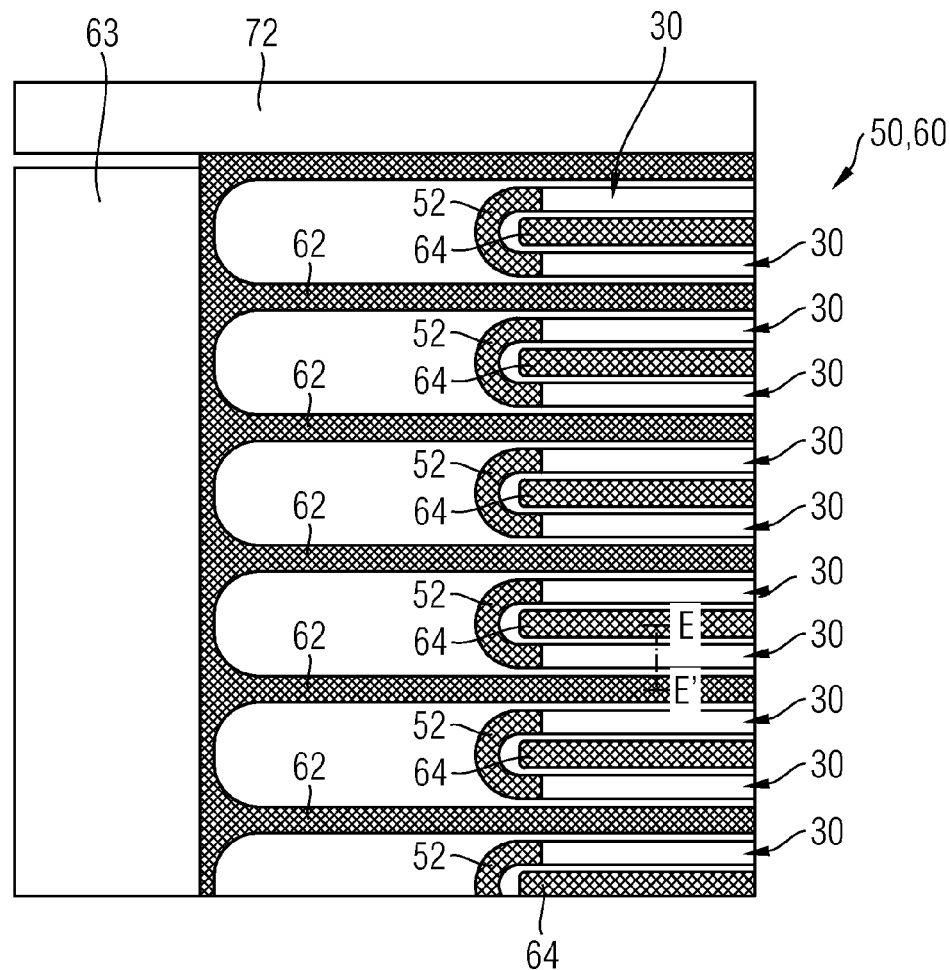
FIG. 7B is a detailed plan view of part $P_2$ of FIG. 6A.
Figure 7C:
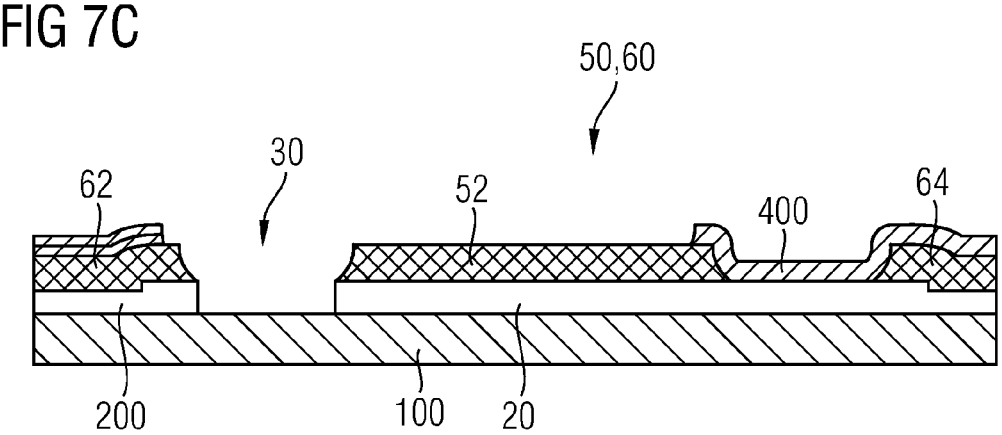
FIG. 7C is a schematic cross-sectional view of a portion of the apparatus for analyzing ion kinetics taken along the section plane E-E' of FIG. 7B.

A detailed view of the part $P_2$ of FIG. 7A is shown in FIG. 7B. As can be seen from FIG. 7B, the ion reservoir 30 is further provided to form a structure as shown in the cross-section along the section plane E-E' of FIG. 7B. As can be seen from FIG. 7C, the structure of the apparatus 10 is comparable to the first part 500 as shown for example in FIG. 3A. By providing the structures as shown in FIG. 6A or FIG. 7A of the apparatus 10, a plurality of first parts 500 as shown in FIG. 3A, 3B or FIG. 5 may be provided, thus enhancing the response of the capacitor structure 50 on mobile ions 40 from the ion reservoir 30. Furthermore, by providing the structure as shown in FIG. 6A, a homogeneous heating of the plurality of dielectric probe structures 20 may be achieved.

In the following, a method for analyzing ion kinetics in the dielectric probe structure 20 of the apparatus 10 will be discussed.

Figure 8:
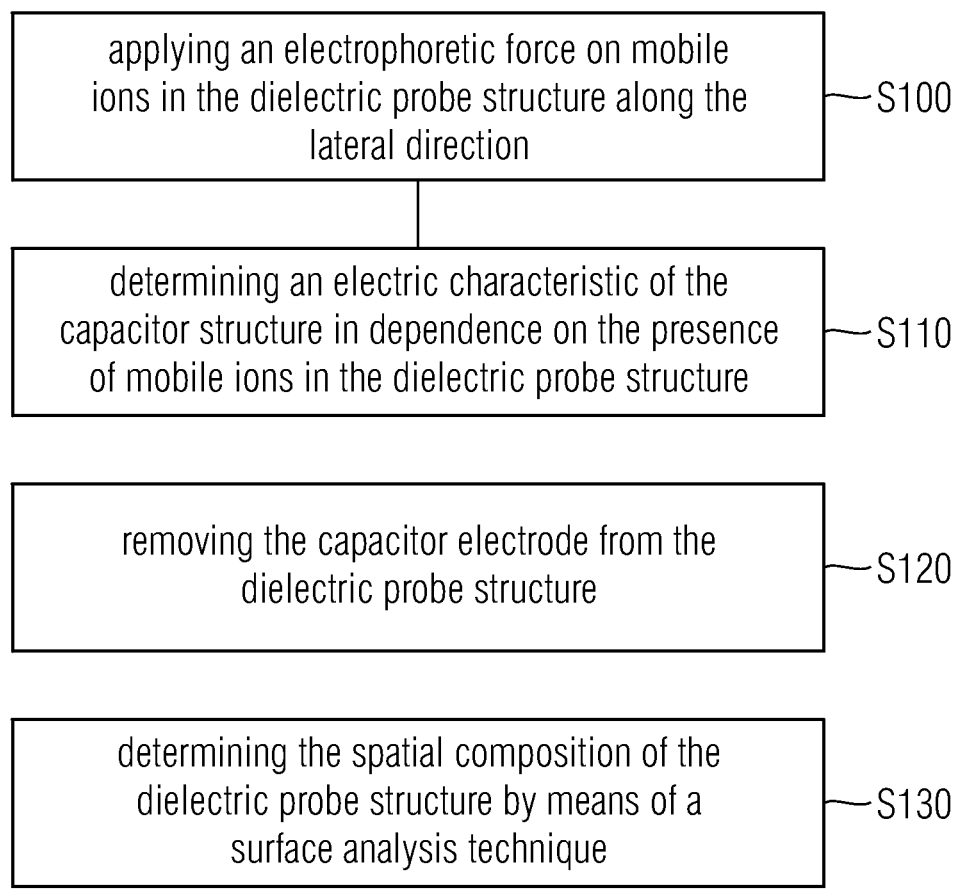
FIG. 8 is a flow chart illustrating a method for analyzing ion kinetics in a dielectric probe structure according to an embodiment.

FIG. 8 shows a flow chart of the method for analyzing ion kinetics according to an embodiment. In a step S100, an electrophoretic force F is applied on mobile ions 40 in the dielectric probe structure 20 along the lateral direction x. In a step S110, an electric characteristic of the capacitor structure 50 in dependence on the presence of mobile ions 40 in the dielectric probe structure 20 is determined. Herein, the electric characteristic of the capacitor structure 50 may be a C-V-characteristic under bias temperature stress, a triangular voltage sweep characteristic, or a temperature stimulated ionic current characteristic of the capacitor structure 50. Further, determining an electric characteristic of the capacitor structure 50 in dependence on the presence of mobile ions 40 in the dielectric probe structure 20 may include determining the characteristic of the MISFET-structure 90 as shown in FIG. 3B. In addition, a compensating current between the first electrode 62 and the second electrode 64, resulting from the mobile ions moving from the ion access area 34 to the second side wall 26 and accumulating at the second side wall 26, may be measured and analysed for determining characteristic parameters of the dielectric probe structure 20 and/or the mobile ions 40. The method may further comprise, according to an embodiment, the step S130 of determining the spatial composition of the dielectric probe structure 20 by means of a surface analysis technique. Therefore, the method may comprise, according to an embodiment, the step S120 of removing the capacitor electrode 52 from the dielectric probe structure 20 to perform the surface analysis technique.

The surface analysis technique may comprise one of a group consisting of secondary ion mass spectroscopy (SIMS), time-of-flight secondary ion mass spectrometry (TOF-SIMS), an Auger electron spectroscopy (AES), X-ray photoelectron spectroscopy (XPS), and X-ray diffraction (XRD).

In detail, a measuring step using the apparatus 10 may be the following. At first, a sample of mobile ions 40 is inserted into the cavity 32 of ion reservoir 30 and a suitable electrical field is applied in a lateral direction x through the dielectric probe structure 20. It is necessary for a proper measurement of ion kinetics in the dielectric probe structure 20 that the dielectric probe structure 20 is substantially free of ion impurities being already present in the dielectric probe structure 20 before measurement. The electrical field in the lateral direction x through the dielectric probe structure 20 may be, at a temperature of 300 K or 500 K in the dielectric probe structure 20, in a range of 1 kV/cm to 10 MV/cm, in a range of 500 kV/cm to 5 MV/cm, or in a range of 1 MV/cm to 3 MV/cm. The distance of the first electrode 62 and the second electrode 64, or the distance between the first side wall 24 and the second side wall 26 of the dielectric probe structure 20 may be in a range of 1 μm to 200 μm. Thus, a voltage in a range of 10 V to 1 kV may be applied between the first electrode 62 and the second electrode 64. In case of an electric field in the lateral direction x of the dielectric probe structure 20 an electrophoretic force F is applied on the mobile ions 40, which starts to move along the lateral direction x.

The transport of mobile ions in insulating materials such as the dielectric probe structure 20 may be thermodynamically enabled by means of driving forces as gradients in the chemical potential (diffusion) or electrical fields (drift). Drift, diffusion or both can be used to transport the mobile ions 40 from the sample in the cavity 32 into the dielectric probe structure 20.

Concerning the diffusion process, caused by chemical gradients, there is the tendency of the mobile ions 40 to have a homogenous distribution throughout the dielectric probe structure 20. This transport can be described by Fick's second law of diffusion, with existing analytical solutions for the situation of having a defined mobile ions source, the ion reservoir 30, at the interface (the ion access area 34) between the mobile ion containing sample and the dielectric probe structure 20. Kinetics of diffusion varies with the species of mobile ion, generally related to their respective ionic radii. Thus, smaller ions diffuse much faster through the dielectric probe structure 20. Diffusion can therefore be enhanced by increasing the temperature in the dielectric probe structure 20. The dielectric probe structure 20 can be designed to be heated for increasing the temperature of the dielectric probe structure 20, e.g. by means of the heater 70.

Concerning the drift process, differences of electric potentials on opposing side walls 24, 26 of the dielectric probe structure 20 may cause an electric field, which may act as a driving force for mobile ion drift. Coupled with diffusion phenomena, there may be a tendency to reach the electrochemical equilibrium. However, generally the drift dominates significantly diffusion, which may cause the mobile ions 40 to be transported towards the side of the dielectric probe structure 20 that exhibit lower electric potential, which may thereby represent the cathode of the system. The electric drift can generally be described by Ohm's law. Treating the dielectric probe structure 20 as a resistor against mobile ion transport, the applied voltage may result in a certain flux of mobile ions 40 towards the cathode, i.e. the second electrode 64.

Using a combination of diffusion and drift in a process termed bias-temperature stress, for example a combination of heating the dielectric probe structure 20 and applying and adjusting a voltage between the first electrode 62 and the second electrode 64, mobile ions 40 of different size and charge will move at different velocities. In this way, different species of mobile ions, such as $Li^+$, $Na^+$, $K^+$, $Ca^{++}$, $Mg^{++}$ and other ions can be separated in a chromatographic process. For such an implementation of the apparatus 10 as a selective ion detecting device, the embodiment of FIGS. 4 and 5 may be useful, in which at least two parts 52a, 52b of the capacitor electrode 52 are provided. In this device, the capacitor structure 50 is spatially separated along the lateral direction x (the moving direction of the mobile ions 40), resulting in spatially resolved determining of electric characteristics of the dielectric probe structure 20 in the lateral direction x. As a result, the dielectric probe structure 20 acts as an electrophoretic carrier for the mobile ions 40 being separately detected by the capacitor structure 50.

As discussed above, the liquid or solid ion solution in the cavity 32 comprising the mobile ions 40 may be a liquid or a solid sample containing earth alkali ions such as $Li^+$, $Na^+$, $K^+$, $Ca^{++}$, $Mg^{++}$ or the like. Also migration of protons $H^+$ may be analysed. These ions are mobile in the sample and to a different extent also in the dielectric probe structure 20 and are therefore referred to as mobile ions 40 herein. As one example, the sample can be liquid samples such as blood or urine and the apparatus 10 may be used for measuring the $K^+$ concentration in blood. The apparatus 10, however, can be equally used for negative ions such as $Cl^-$, $F^-$, or $OH^-$. The liquid sample may be, for example, water, drinking water, beverage, electrolyte solution, wastewater, a body liquid such as blood, urine or any other type of liquid, and the apparatus can be used for specifically determining an ion concentration in the sample.

The mentioned approach for measuring the quantity of mobile ions may be applied in medicinal measurements as e.g. $K^+$ in blood samples. This may enable the measurement of the K+ concentration in the blood sample, which may be described in mmol/l (millimole per liter of liquid sample). According to one specific example, a homogeneous K+ concentration in a blood sample may be ~4 mmol/l (i.e. ~10 ppm or ~1E18 ions/cm$^3$).

For determining the diffusion characteristics of predetermined mobile ions 40 in a dielectric probe structure 20 chosen to be investigated, the mobile ions 40 may diffuse below the capacitor electrode 52 along the electric field in the lateral direction x, which is generated by in-situ electrodes 62, 64. By means of a measurement of capacity, the migration of the mobile ions 40 under the capacitor electrode 52 may be measured due to a change in electric characteristic of the capacitor structure 50, thus a diffusion velocity of the mobile ions 40 within the selected dielectric probe structure 20 may be determined. The electric characteristic may be a change of the C-V-characteristic of the capacitor structure 50 consisting of the capacitor electrode 52, the dielectric probe structure 20, the dielectric base structure 22, the semiconductor body 100 and the back electrode 54. However, it is also possible to provide a metal-insulator-metal structure comprising the capacitor electrode 52, the dielectric probe structure 20 and a metal layer being provided between the semiconductor body 100 and the dielectric structure 200. Furthermore, a conductive body may be chosen instead of the semiconductor body 100. The diffusion and/or drift parameters of the mobile ions 40 may be determined by employing an Arrhenius-plot-technique or finite difference-algorithms.

According to an embodiment, the determining of the electric characteristic of the capacitor structure 50 may be combined with determining of the spatial composition of the dielectric probe structure 20 by means of a surface analysis technique. The capacitor electrode 52 may be stripped from the surface of the dielectric probe structure 20 to provide access to the dielectric probe structure 20 for a physical measurement technique. According to one embodiment, the surface analysis technique may comprise a time-of-flight secondary ion mass spectrometry (TOF-SIMS), in which the composition of the dielectric probe structure 20 may be determined by spatially ablating this structure, e.g. by sputtering, and analysing the composition of the dielectric probe structure 20. Thus, the exact position of the mobile ions 40 and the respective ion type may be determined after performing of the electrophoretic process in the dielectric probe structure 20. By comparison of the two different signals of the electric characteristic and the surface analysis technique, the diffusion characteristic of the mobile ions 40 in the respective dielectric probe structure 20 may be determined. Optionally, the capacitor electrode 52 may be chosen smaller in its lateral dimension as necessary for physical measurement. This may be of advantage if measurements are performed under high electric fields. Variable measurement parameters are the temperature and the potential difference between the electrodes 62, 64. The embedding of the first part 500 within the heater 70 further allows an additional quick and independent heating and cooling process. Thus, the measurement temperature may be set in very short times, leading to the possibility of quenching the transport process of the mobile ions 40 within the dielectric probe structure 20.

By means of the method described above for analyzing ion kinetics in the dielectric probe structure 20, both electrical characteristic data and surface analysis data may be applied. The surface analysis is facilitated by performing the measurement of electrical characteristic data in a vertical direction z and having the movement direction of the mobile ions 40 in a lateral direction x. Thus, a surface analysis of the dielectric probe structure 20 may be easily performed by stripping the capacitor electrode 52 or the capacitor electrode parts 52a, 52b. In addition, artefacts of migration may be prevented by the structure of the apparatus 10. In summary, both measurement principles are combined in one arrangement. By means of the MOS-structure of the capacity structure 50, an additional time resolved electrical signal of the ion drift in form of a variable capacity characteristic is received, wherein the measurement of the electrical characteristic may be easily combined with the measurement of the physical characteristic, i.e. the determining of the spatial composition of the dielectric probe structure 20 by means of a surface analysis technique.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An apparatus for analyzing ion kinetics, comprising:
a dielectric structure including any dielectric or combination of dielectric materials having ion transport characteristics;
an ion reservoir abutting the dielectric structure and configured to supply mobile ions to the dielectric structure;
a capacitor structure configured to generate an electric field in the dielectric structure along a vertical direction;
an electrode structure configured to generate an electrophoretic force on mobile ions in the dielectric structure along a lateral direction: and
a sample reservoir configured to receive a sample liquid or ion solution.

2. The apparatus of claim 1, wherein the capacitor structure comprises a metal insulator semiconductor field effect transistor structure.

3. The apparatus of claim 1, wherein the capacitor structure comprises:
a semiconductor body, the dielectric structure being disposed on the semiconductor body; and
a capacitor electrode on the dielectric structure.

4. The apparatus of claim 3, wherein the capacitor electrode comprises at least two capacitor electrode parts each being separated in the lateral direction.

5. The apparatus of claim 3, wherein the capacitor structure further comprises a dielectric base structure between the semiconductor body and the dielectric structure.

6. The apparatus of claim 5, wherein the dielectric structure and the dielectric base structure are parts of a dielectric structure, in which the dielectric structure is a patterned dielectric body protruding along the vertical direction from the dielectric base structure.

7. The apparatus of claim 1, wherein the electrode structure comprises:
a first electrode located next to the ion reservoir at a first side wall of the dielectric structure; and
a second electrode located at a second side wall of the dielectric structure.

8. The apparatus of claim 3, wherein the electrode structure comprises a first electrode located next to the ion reservoir at a first side wall of the dielectric structure, and a second electrode located at a second side wall of the dielectric structure, and wherein the capacitor electrode, the first electrode and the second electrode are parts of a patterned electrode layer structure.

9. The apparatus of claim 8, wherein the patterned electrode layer structure comprises at least one element selected from the group consisting of Al, Cu, AlSi, AlCu and AlSiCu.

10. The apparatus of claim 1, wherein the dielectric structure comprises at least one element selected from the group consisting of silicon oxide $SiO_2$, silicon oxynitride $SiO_xN_y$, and amorphous silicon nitride containing hydrogen or deuterium a-$Si_xN_yH_z$/$Si_xN_yD_z$.

11. The apparatus of claim 1, wherein a dimension of the dielectric structure in the lateral direction is in a range of 1 μm to 200 μm and a dimension of the dielectric structure in the vertical direction is in a range of 10 nm to 1 μm.

12. The apparatus of claim 1, wherein the sample reservoir comprises a cavity in the ion reservoir comprises a cavity that is extended through the dielectric structure along the vertical direction, the cavity being configured to receive a liquid or solid ion solution.

13. The apparatus of claim 12, wherein the cavity has a diffusion barrier layer lining an inner wall of the cavity and at least one ion access area configured to provide access for mobile ions to the dielectric structure.

14. The apparatus of claim 1, wherein the mobile ions comprise one element selected from the group consisting of $H^+$, $Li^+$, $Na^+$, $K^+$, $Ca^{++}$ and $Mg^{++}$.

15. The apparatus of claim 1, wherein the dielectric structure is heatable by a heater.

16. The apparatus of claim 15, wherein the heater comprises a heating conductive layer which is part of the electrode structure.

17. The apparatus of claim 15, wherein the capacitor structure and the electrode structure are arranged in a meandering form, wherein the heater is arranged between a meandering path of the capacitor structure and the electrode structure.

18. The apparatus of claim 15, wherein the electrode structure comprises two finger electrode structures interlacing with each other in parallel, the capacitor structure is arranged in a meandering form such that the two finger electrode structures further interlace with the capacitor structure, and the heater is arranged next to the two finger electrode structures and the capacitor structure.

19. The apparatus of claim 1, wherein the sample reservoir comprises a cavity in the dielectric structure.

20. A method for analyzing ion kinetics in a dielectric structure of an apparatus comprising the dielectric structure including any dielectric or combination of dielectric materials having ion transport characteristics, an ion reservoir abutting the dielectric structure and configured to supply mobile ions to the dielectric structure, a capacitor structure configured to generate an electric field in the dielectric structure along a vertical direction, and an electrode structure configured to generate an electrophoretic force on mobile ions in the dielectric structure along a lateral direction, the method comprising:
   applying an electrophoretic force on mobile ions in the dielectric structure along the lateral direction; and
   determining an electric characteristic of the capacitor structure based on the presence of mobile ions in the dielectric structure.

21. The method of claim 20, wherein the electric characteristic of the capacitor structure is a C-V-characteristic under bias temperature stress, a triangular voltage sweep characteristic, or a temperature stimulated ionic current characteristic of the capacitor structure.

22. The method of claim 20, further comprising:
   determining a spatial composition of the dielectric structure by means of a surface analysis technique.

23. The method of claim 22, further comprising:
   removing, before determining the spatial composition of the dielectric structure by means of a surface analysis technique, the capacitor electrode from the dielectric structure.

24. The method of claim 22, wherein the surface analysis technique is selected from the group consisting of secondary ion mass spectrometry (SIMS), Time-of-flight secondary ion mass spectrometry (TOF-SIMS), Auger electron spectroscopy (AES), X-Ray Photoelectron Spectroscopy (XPS), and X-ray diffraction (XRD).

* * * * *